US00PP30065P2

(12) United States Plant Patent
Verhoef

(10) Patent No.: US PP30,065 P2
(45) Date of Patent: Jan. 8, 2019

(54) ***WEIGELA* PLANT NAMED 'ZR1'**

(50) Latin Name: *Weigela florida*
Varietal Denomination: ZR1

(71) Applicant: Gijsbertus Verhoef, Hazerswoude-Dorp (NL)

(72) Inventor: Gijsbertus Verhoef, Hazerswoude-Dorp (NL)

( * ) Notice: Subject to any disclaimer, the term of this patent is extended or adjusted under 35 U.S.C. 154(b) by 0 days.

(21) Appl. No.: 15/732,427

(22) Filed: Nov. 9, 2017

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Weigela florida*, 'ZR1', characterized by its very compact plant habit, its foliage that is dark purple-black in color, its floriferous and remontant blooming habit, and its flowers that are red-purple in color.

2 Drawing Sheets

Botanical classification: *Weigela florida.*
Variety denomination: 'ZR1'.

BACKGROUND OF THE INVENTION

The present invention relates to a new and distinct cultivar of *Weigela* and will be referred to hereafter by its cultivar name, 'ZR1'. 'ZR1' represents a new cultivar of *Weigela*, a deciduous shrub grown for landscape use.

The new cultivar originated as a seedling in a trial field that was planted with seeds derived from open pollination of *Weigela* 'Tango' (not patented) in Hazerswoude-Dorp, The Netherlands. The pollen parent is therefore unknown. 'ZR1' was selected as a single unique plant by the Inventor in July of 2008.

Asexual propagation of the new cultivar was first accomplished by softwood stem cuttings by the Inventor in June of 2009 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'ZR1' as a unique cultivar of *Weigela.*

1. 'ZR1' exhibits a very compact plant habit.
2. 'ZR1' exhibits foliage that is dark purple-black in color.
3. 'ZR1' exhibits a floriferous and remontant blooming habit.
4. 'ZR1' exhibits flowers that are red-purple in color.

The seed parent of 'ZR1', 'Tango', differs from 'ZR1' in having a less compact plant habit, in having foliage that is much lighter in color and flowers that are pink-purple in color. 'ZR1' can also be compared to the *Weigela florida* cultivars 'Verweig 3' (not patented) and 'Elvera' (U.S. Plant Pat. No. 12,217). Both 'Verweig 3' and 'Elvera' are similar to 'ZR1' in having foliage that is dark purple-black in color. 'Verweig 3' differs from 'ZR1' in having leaves that are larger in size, foliage that is lighter in color and flowers that are purple-pink color. 'Elvera' differs from 'ZR1' in being much less floriferous and in having flowers that are purple in color.

BRIEF DESCRIPTION OF THE DRAWINGS

The accompanying colored photographs were taken in August and illustrates the overall appearance and distinct characteristics of 14 month-old plants the new *Weigela* as grown outdoors in a field Hazerswoude-Dorp, The Netherlands.

The photograph in FIG. 1 provides an overall view of the plant habit of 'ZR1'.

Figure 1:
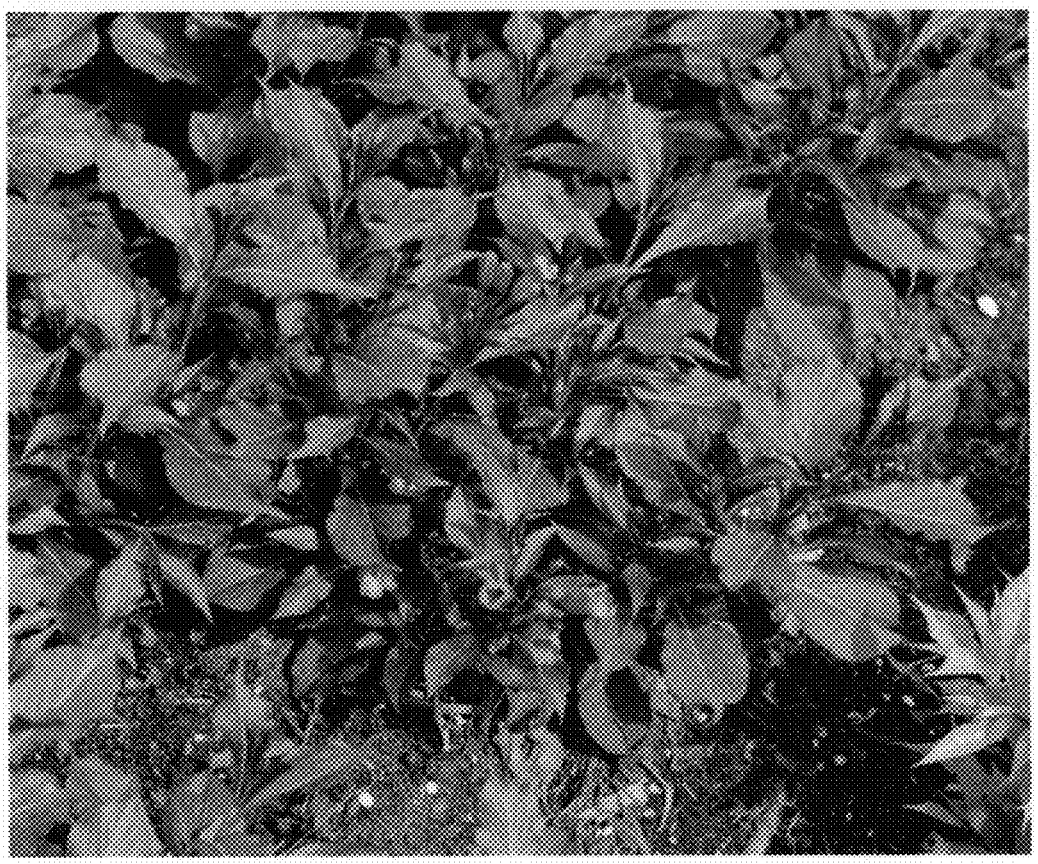
Figure 2:
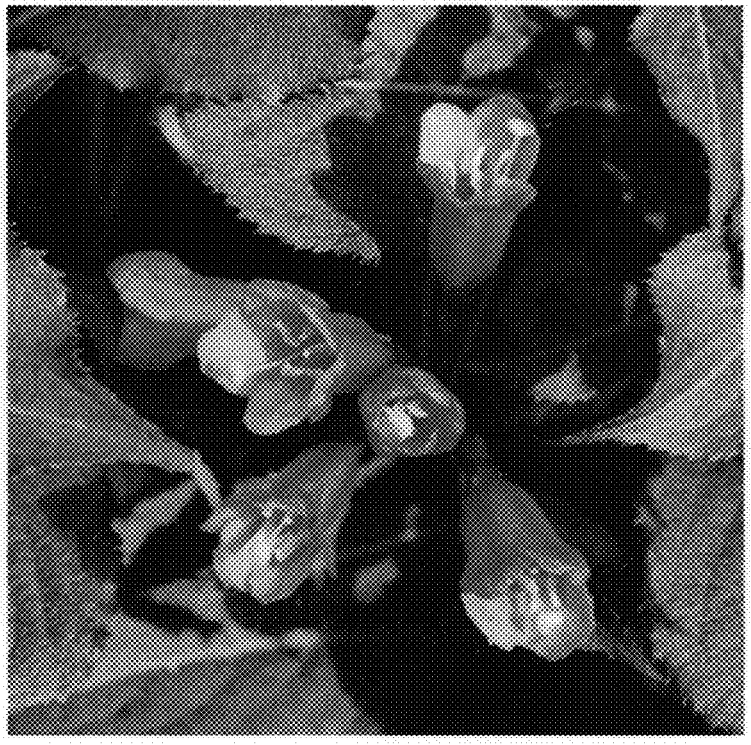

The photograph in FIG. 2 provides a close-up view of the flowers of 'ZR1'.

Figure 3:
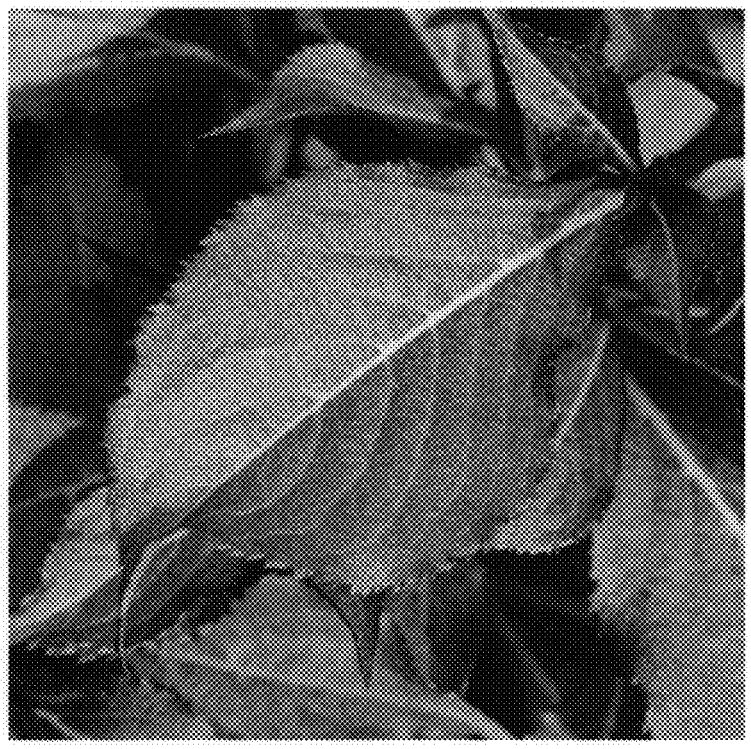

The photograph in FIG. 3 provides a close-up view of the foliage of 'ZR1'.

The colors in the photograph may differ slightly from the color values cited in the detailed botanical description, which accurately describe the colors of the new *Weigela.*

DETAILED BOTANICAL DESCRIPTION

The following is a detailed description of 14 month-old plants of the new cultivar as grown outdoors in a field in Hazerswoude-Dorp, The Netherlands. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period.*—Remontant; in late spring (May) and late summer to early fall (August to September) in The Netherlands.

*Plant type.*—Deciduous flowering shrub.

*Plant habit.*—Very compact, broadly upright and spreading, freely branched.

*Plant size*.—Reaches about 34.7 cm in height and 38.4 cm in width as a 14 month-old plant and 60 cm in height and 125 cm in width as a mature plant in the landscape.

*Cold hardiness*.—At least in U.S.D.A. Zone 5.

*Diseases and pests*.—No susceptibility to resistance to diseases or pests has been observed.

*Root description*.—Fibrous, moderately dense.

*Propagation*.—Softwood stem cuttings.

*Root initiation*.—An average of 6 weeks.

*Root development*.—An average of 3 months to produce a young rooted plant.

*Growth rate*.—Moderate.

Branch description:

*Branch shape*.—Moderately quadrangular.

*Branch color*.—New growth; between 148A and 197A, 200B, mature wood; 187B, bark; 200B.

*Branch size*.—An average of 12.3 cm in length and 2 mm in diameter.

*Branch surface*.—New growth; slightly glossy, sparsely covered with short hairs an average of 0.3 mm in length and too small to measure color.

*Branch aspect*.—Upright to outward at an average angle of 35°.

*Branch strength*.—Moderately strong.

*Branching*.—An average of 8 main basal branches and 56 lateral branches.

*Internode length*.—Average of 3 cm.

Foliage description:

*Leaf shape*.—Obovate.

*Leaf division*.—Simple.

*Leaf base*.—Attenuate.

*Leaf apex*.—Apiculate to near cuspidate.

*Leaf fragrance*.—None.

*Leaf aspect*.—Flat to slightly carinate, tip is moderately twisted and pointed downward in an average angle of 60° to leaf blade.

*Leaf venation*.—Pinnate, color upper surface 151A, color lower surface a color between 152D and tinged 138D.

*Leaf margins*.—Serrate.

*Leaf arrangement*.—Opposite.

*Leaf attachment*.—Petiolate.

*Leaf surface*.—Both surfaces slightly rugose, smooth and glabrous, upper surface; main veins moderately covered with soft pubescence an average of 0.2 mm in length and 156D in color, lower surface; main vein moderately covered with very short hairs average of 0.5 mm in length and too small to measure color.

*Leaf size*.—An average of 7.8 cm in length and 4.1 cm in width.

*Leaf quantity*.—An average of 10 (5 pairs) per lateral branch.

*Leaf color*.—Young upper surface; between 200A and 203B, young lower surface; 200A, mature upper surface; between 147A and 200A, mature lower surface; 200B, tinged 147B and N186C.

*Petioles*.—Average of 5 mm in length, 2.5 mm in width, upper surface color 151C, margins N200A, lower surface color 152D, tinged 183D, strong.

*Stipules*.—None.

Inflorescence description:

*Inflorescence type*.—Solitary, in pairs, or in small clusters at terminus and leaf axils.

*Inflorescence size*.—5.3 cm in height, 3.8 cm in diameter.

*Flower buds*.—Oblanceolate in shape, an average of 2.4 cm in depth and 7 mm in diameter, 185A, tip is 185B in color, surface is matte, smooth and glabrous.

*Flower fragrance*.—None.

*Lastingness of flowers*.—About 12 days, self-cleaning.

*Flower aspect*.—Outward to slightly upright.

*Flower quantity*.—An average of 7 per inflorescence, 375 buds and flowers per plant.

*Flower type*.—Tubular.

*Flower size*.—Average of 1.3 cm in height, 1.4 cm in diameter, 3.2 cm in depth, throat; 9 mm in diameter, tube; 2.2 cm in length, 8 mm in diameter.

*Peduncles*.—Average of 5 mm in length and 1 mm in diameter, held straight on top of lateral branch, moderately strong, slightly glossy and sparsely covered with short strigose hairs; average of 0.3 mm in length and too small to measure color.

*Calyx*.—Rotate in shape, an average of 1 cm in depth and 5 mm in width.

*Sepals*.—5, rotate, linear in shape, narrowly acute apex, cuneate base, entire margin, an average of 1 cm in length and 1 mm in width, lower 30% fused, both surfaces smooth, glabrous and moderately glossy, color; when opening and fully open upper surface 181B and fading towards the tip to 200A, when opening and fully open lower surface 178A and fading towards the tip to 200A.

*Petals*.—5, lower 70% fused into tube, spathulate in shape, margin entire on free portion, apex obtuse, an average of 2.8 cm in length, 7 mm in width, upper and lower surface glabrous and slightly velvety, color; when opening upper surface 185B, when opening lower surface a color between 46A and 185B, when fully open upper surface a color between 53B and 185B, when fully open lower surface a color between 46A and 185B, throat a color between 53C and 185B, flower tube color 185B, lower side a color between 53A and 185A.

Reproductive organs:

*Gynoecium*.—Pistil; 1, average of 2.5 cm in length, style; average of 2.4 cm in length, and 196D, fading towards proximal end to 182C in color, stigma; club-shaped, 1 mm in length and 2 mm in diameter, 195B in color, ovary; 177B in color.

*Androecium*.—Stamens; 5, filaments; 65D, fading towards the base to 61D in color and an average of 1.2 cm in length, implanted in petals, anthers; NN155B in color, an average of 4 mm in length, 0.5 mm in width, narrowly oblong in shape, pollen; moderate in quantity and 11D in color.

*Fruit and seed*.—No fruit or seed production has been observed to date.

It is claimed:

1. A new and distinct cultivar of *Weigela* plant named 'ZR1' as herein illustrated and described.

* * * * *